US006978787B1

(12) United States Patent
Broniatowski

(10) Patent No.: US 6,978,787 B1
(45) Date of Patent: Dec. 27, 2005

(54) METHOD AND SYSTEM FOR DYNAMIC VOCAL FOLD CLOSURE WITH NEURO-ELECTRICAL STIMULATION

(76) Inventor: Michael Broniatowski, 2646 Fairmont Blvd., Cleveland, OH (US) 44106

( * ) Notice: Subject to any disclaimer, the term of this patent is extended or adjusted under 35 U.S.C. 154(b) by 745 days.

(21) Appl. No.: 10/115,803

(22) Filed: Apr. 3, 2002

(51) Int. Cl.[7] .............................................. A61B 19/00
(52) U.S. Cl. ...................................................... 128/898
(58) Field of Search ........................... 128/898; 607/72, 607/42, 40

(56) References Cited

U.S. PATENT DOCUMENTS 5,725,564 A * 3/1998 Freed et al. ................... 607/72
5,897,579 A * 4/1999 Sanders ........................ 607/42

OTHER PUBLICATIONS

Article published as follows: Dynamic Laryngotracheal Closure for Aspiration: A Preliminary Report By: Michael Broniatowski, MD, FACS In: Laryngoscope 111: Nov. 2001 pp. 2032–2040 Two copies are provided, one that has photos that are hard to distinguish and the other with better photos. Although there are others listed in the paper, they are not inventors.

\* cited by examiner

*Primary Examiner*—George C. Manuel
*Assistant Examiner*—Lenwood Faulcon, Jr.
(74) *Attorney, Agent, or Firm*—Frank Cozzarelli, Jr.; Cozzarelli Law Firm

(57) ABSTRACT

A method and system for treating dysphagia using electrical stimulation of a human's or animals's vagus nerve, or recurrent laryngeal nerve, or both to cause glottic or vocal fold motion in humans or animals. Stimulation is caused by utilizing a power source; an external controller for generating and providing an output signal having a given intensity, frequency, and pulse duration; an output protector circuit for limiting the intensity of the output signal; a treatment duration circuit for controlling the duration of operation of the external controller, a ramp control circuit for controlling the intensity of the output signal; and a monitor portion for displaying operating parameters of the device. The external controller regulates the intensity, the frequency, and the pulse duration of the output signal in accordance with a procedure for treating dysphagia.

7 Claims, 2 Drawing Sheets

SECTION AT 1—1

METHOD AND SYSTEM FOR DYNAMIC VOCAL FOLD CLOSURE WITH NEURO-ELECTRICAL STIMULATION

TECHNICAL FIELD

The present invention relates to a method and system that dynamically treats the upper airway by electrical stimulation of the nerves to the vocal folds, i.e. the vagus or its branch, the recurrent laryngeal nerve (RLN) to cause adduction (closure) of the vocal folds of humans or animals while protecting the upper airways. Strong closure of the vocal folds, vagus or RLN by electrical stimulation reduces aspiration of solids and liquids into the windpipe and assists in swallowing.

BACKGROUND OF THE INVENTION

According to the National Stroke Association, 550,000 Americans suffer a new or recurrent stroke each year. Of these patients, nineteen percent (19%) to thirty eight percent (38%), or about 150,000, will aspirate, which is defined as the taking of foreign material, such as saliva and ingested food, into the lungs. Aspiration increases the chances of contracting pneumonia by 20-fold and is believed responsible for approximately 40,000 deaths following a stroke every year in the United States alone.

Aspiration results from several factors, including insufficient laryngeal elevation, poor coordination of pharyngeal muscular contraction, and/or insufficient or untimely and poorly adjusted closure of the vocal folds to protect the airway. If standard therapies fail, the patient may not be allowed to take food by mouth and tubes may have to be placed into the intestinal tract to bypass swallowing. Current options to protect the airways involve irreversible and destructive surgery of the upper airway. These often reduce the patient's quality of life.

Swallowing is normally initiated according to a series of steps of the oral phase such as the introduction of food into the mouth, mastication, posterior tongue thrusting, and so on. Once the bolus is present in the pharynx, however, the process becomes fully reflexogenic as it automatically proceeds until an end point represented by laryngeal closure and bolus diversion through the opening upper esophageal sphincter acting as a suction pump.

While brain plasticity allows many patients to regain workable function within a few weeks, aspiration persists beyond this period in approximately one half of the cases. Some treatments include special risk-reduction diets with varied consistency, composition, and calorie counts delivered in conjunction with passive measures (e.g. chin tuck, head turn, double supraglottic swallow, supersupraglottic swallow, the Mendelsohn maneuver, and so on). These patients often require a tracheotomy to secure pulmonary toilet and enteral feedings (i.e. not natural, by external means into the gut) such as through tube gastrostomy or jejunostomy to deliver appropriate caloric intake. Despite such precautions, pneumonia will still occur in approximately twenty percent (20%) of the cases.

Whatever the nature of the disruption affecting the pharyngeal sequence leading to laryngeal incompetence after various neurological assaults and not alleviated by non-invasive approaches, therapy has focused on surgical separation between the airway and the alimentary tract to either seal the airway or to divert the passage of ingested material away from the incompetent laryngeal valve and prevent flooding of the lungs. While there has traditionally been no alternative, these interventions have a major disadvantage in that they must mutilate normal organ systems, i.e., the larynx and the pharynx, often irreversibly, to be clinically effective. Moreover, these operations have an additional disadvantage in that they lack the dynamic qualities required for the restoration of the mutually exclusive functions of vocal fold adduction, which is necessary for speaking and swallowing, and abduction (opening of the vocal folds), which is necessary for breathing, thus imposing a choice between airway safety and voice production It is, therefore, desirable to have a simple, dynamic method and system that does not mutilate normal organs such as the larynx and the pharynx to restore the ability to swallow in humans or animals.

SUMMARY OF THE INVENTION

With the above limitations of the current approaches in mind, it is an object of the present invention to provide a method and system that dynamically treats the upper airway by electrical stimulation of either one or both of the vagus nerves or recurrent laryngeal nerves (RLN) to cause adduction of the vocal folds of humans or animals. Electrical stimulation of the vagus or RLN nerves produces strong vocal fold closure (glottic fold motion), reduces aspiration of solids and liquids, thus assisting swallowing.

These and additional benefits of the present invention will become clear from the following description.

An object of the present invention is to provide a method and system that dynamically treats the upper airway by vagus or recurrent laryngeal nerve (RLN) electrical stimulation to cause vocal fold adduction (glottic fold motion) in humans or animals. Vagal or RLN stimulation produces strong vocal fold closure, reduces aspiration of solids and liquids, and assists in swallowing without mutilating and causing irreversible and destructive surgery to the upper airway and normal organ systems, i.e., the larynx and the pharynx.

Another object of the present invention is to provide a method and system that dynamically treats the upper airway by vagal or recurrent laryngeal nerve (RLN) electrical stimulation to cause vocal fold adduction in humans or animals that does not impose a choice between airway safety and voice production.

Another object of the present invention is to provide a method and system that dynamically treats the upper airway by vagal or recurrent laryngeal nerve (RLN) electrical stimulation to cause vocal fold adduction in humans or animals that focuses on aspiration, which is as yet not satisfactorily controlled. electrical stimulation to cause vocal fold adduction in humans or animals that is an all-encompassing device completely bypassing an abolished function for which it provides a dynamic substitute.

Another object of the present invention is to provide a method and system that dynamically treats the upper airway by recurrent laryngeal nerve (RLN) electrical stimulation to cause vocal fold adduction in humans or animals that allows the subject to be independent of external electrical connections as long as the device is electrically charged.

The objects, advantages and features of the present invention are readily apparent from the following description of the preferred embodiment for carrying out the invention when taken in connection with the accompanying drawings. In accordance with the present invention entitled, Method and System For Dynamic Vocal Fold Closure With Neuro-Electrical Stimulation, there is provided a method and system that dynamically protects the upper airway by vagal or recurrent laryngeal nerve (RLN) electrical stimulation to cause vocal fold adduction in humans or animals, and thus promoting safe swallowing. The method comprising selectively placing at least one perineural electrode in contact with one or both vagus nerves or recurrent laryngeal nerves (RLN), to conduct a series of electrical pulses to stimulate and cause vocal fold adduction and blocking or reducing aspiration of solids and liquids, to assist in swallowing.

The system includes an external controller that programs and transmits electrical pulses to an external transmitter through a transmitter lead. The external transmitter is placed on the patient's skin and transmits pulses via induction to a receiver stimulator that is implanted into a pocket in the patient's chest wall. The receiver stimulator transmits the pulses through a perineural electrode that is implanted in either the right or left side of the patient's neck and then wrapped around either of the vagus or recurrent laryngeal (RLN) nerves. An external battery charger is provided to charge the batteries in the external controller. The external controller is a pulse rate modulator having a frequency generally ranging between 20–60 Hertz, a pulse width of 20 to 200 microseconds, and 0.1 to 2.0 milliAmperes.

In an FDA-approved study (IDE #G980179 assigned to the inventor), general anesthesia was administered and the patient's left recurrent laryngeal nerve (RLN) was identified by electrical stimulation using a commercially available, disposable stimulator (Varistim III, Clearwater, Fla.). Then a perineural electrode was implanted around the RLN and secured, and the leads were tunneled beneath the skin of the neck over the collar bone (clavicle) to the chest wall and linked to an implanted receiver stimulator placed subcutaneously in a pocket on the chest wall through a horizontal incision. Activation of the implanted receiver stimulator was performed transcutaneously using the external transmitter linked by induction. Verification of the effectiveness of the system was confirmed and the incisions were closed, and each patient was monitored for progress.

The study was conducted at St. Vincent's Charity Hospital, Cleveland, Ohio.

DESCRIPTION OF THE PREFERRED EMBODIMENT(S)

Figure 1:
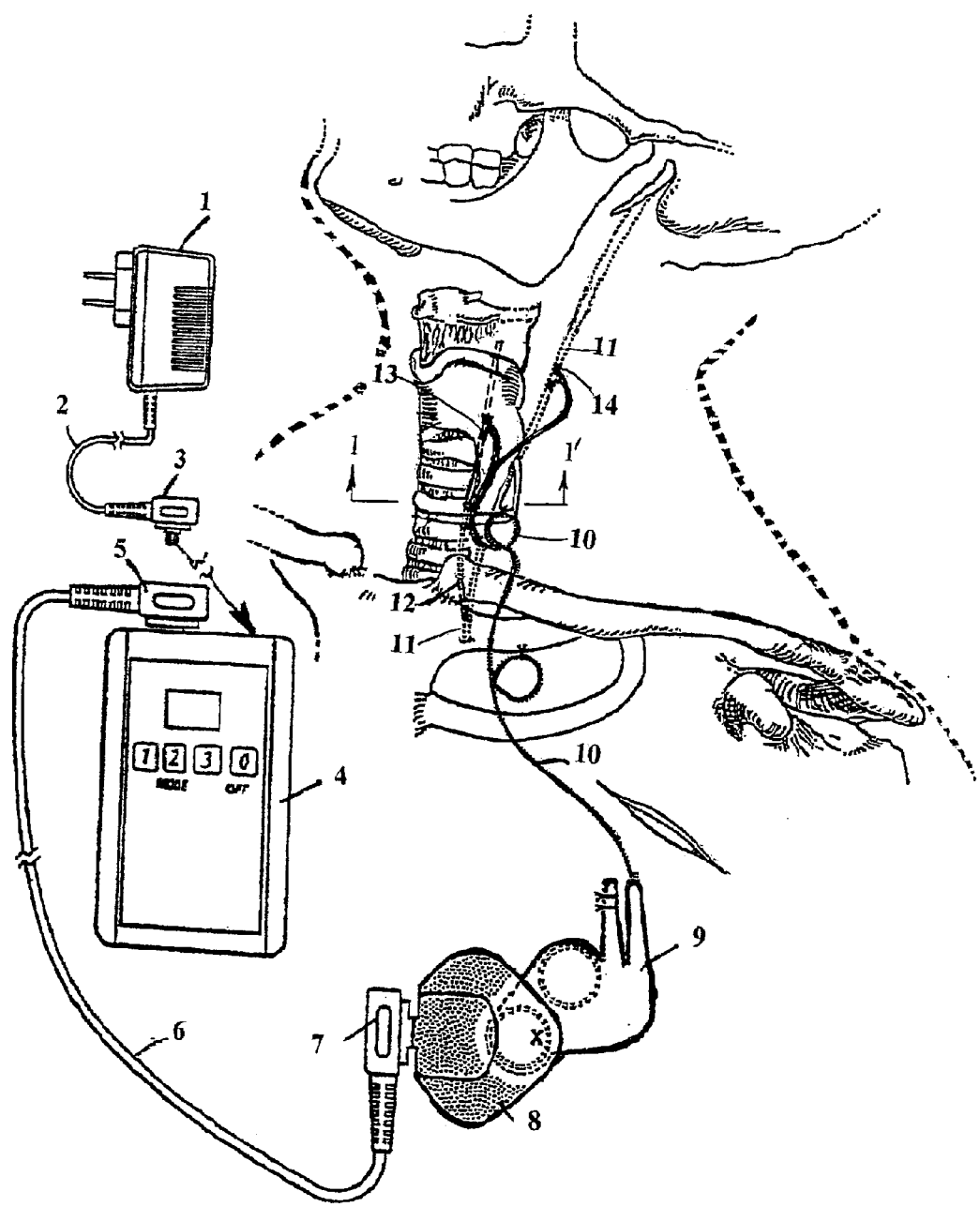
FIG. 1 is a diagrammatic view of a method and system for dynamic vocal fold closure with neuro-electrical stimulation as placed in and externally on a human patient.

A more complete appreciation of the invention and many of the attendant advantages and features thereof may be readily understood by reference to the following more detailed description of the drawings in which like reference characters indicate corresponding parts in all views and the detailed description.

According to a study by the US Department of Health and Human Services in March 1999 there are currently more than 500,000 new cases of cerebrovascular accidents ([CVA], stroke) each year in the United States. This problem is associated with dysphagia and aspiration in approximately one half of the cases from an inability of the damaged central nervous system (CNS) to coordinate the swallowing mechanism. The ensuing combinations of oral apraxia, faulty hyolaryngeal elevation, and decreased laryngeal sensation may be variably expressed on contrast studies videofluoroscopy or modified barium swallow [MBS] as delays in bolus transfer from the mouth to the pharynx, shorter laryngeal elevation and closure, as well as shorter cricopharyngeal opening times as compared with normal subjects. Patients may die from aspiration pneumonia, which can be predicted on the basis of increased pharyngeal pooling, reduced hyolaryngeal elevation, and lengthy oropharyngeal transit times documented either radiologically or through video and endoscopic swallowing studies.

While brain plasticity (the capability for the brain to spontaneously recover) allows most patients to regain workable function within a few weeks, aspiration persists beyond this period in approximately one half of the cases. Strategies used by speech language pathologists to control the problem include special risk-reduction diets with varied consistency, composition, and calorie counts delivered in conjunction with passive measures (e.g. chin tuck, hear turn, double supraglottic swallow, supersupraglottic swallow, the Mendelsohn maneuver, and so on). These patients often require a tracheotomy to secure pulmonary toilet and enteral feedings (i.e. not via the natural paths) through tube gastrostomy and jejunostomy to deliver appropriate caloric intake. It has been estimated that despite such precautions, pneumonia will still occur in approximately 20% of cases.

Whatever the nature of the disruption affecting the pharyngeal sequence leading to laryngeal incompetence after various neurological assaults, therapy has focused on surgical separation between the airway and the alimentary tract to either seal the airway or the divert the passage of ingested material away from the incompetent laryngeal valve and prevent flooding of the lungs. While there has traditionally been no alternative, these interventions have a major drawback in that they must mutilate normal organ systems, i.e., the larynx and the pharynx, often irreversibly, to be clinically effective. Moreover, these operations lack the dynamic qualities required for the restoration of the physiological mutually exclusive functions of vocal fold adduction (necessary for voice and swallowing) and abduction (necessary for breathing), thus imposing a choice between airway safety and voice production at which expense the former is gained.

Because neurologically induced laryngeal incompetence stems from causes extraneous to the otherwise healthy organ, it appears logical to bypass the faulty central nervous system (CNS) to allow a return of working vocal fold adduction affecting an appropriate glottic seal. Preliminary studies done in canine models have demonstrated that neuroprosthetic devices could be used to this effect. Successful restoration of function in clinically unrelated fields (functional electrical stimulation [FES]), such as for voiding and diaphragmatic pacing, using ongoing progress in circuit miniaturization have encouraged applications in otolaryngology—head and neck surgery.

In FIG. 1 is a diagrammatic view of a method and system for dynamic vocal fold closure with neuro-electrical stimulation as placed in and externally on a human patient.

The Dynamic Vocal Fold Closure System, as placed in a human, comprises an external controller (4) having a ramp control circuit that programs and transmits electrical pulses to an external transmitter (8) through a transmitter lead (6). The external transmitter (8) is placed over the patient's skin (i.e. outside the body) and transmits pulses via induction to a receiver stimulator (9) that is implanted into a pocket over the patient's chest wall. The receiver stimulator (9) transmits the pulses through an electrode lead (10) that is also implanted, and tunneled between the chest wall and the neck over the collar bone (clavicle). The perineural electrode (13) or (14) is then wrapped around the vagus nerve (11), or recurrent laryngeal nerve (RLN) (12) or both. An external battery charger (1) is provided to charge the batteries in the external controller (4). The external controller (4) having a ramp control circuit is a pulse generator having a frequency generally ranging between 20–60 Hertz, a pulse width 20 and 300 microseconds, and 0.1 to 2.0 milliamperes In FIG. 2 is a diagrammatic view of section 1-1' of FIG. 1 illustrating the electrode lead (10) near the tracheal wall.

Figures 2, 3, 4:
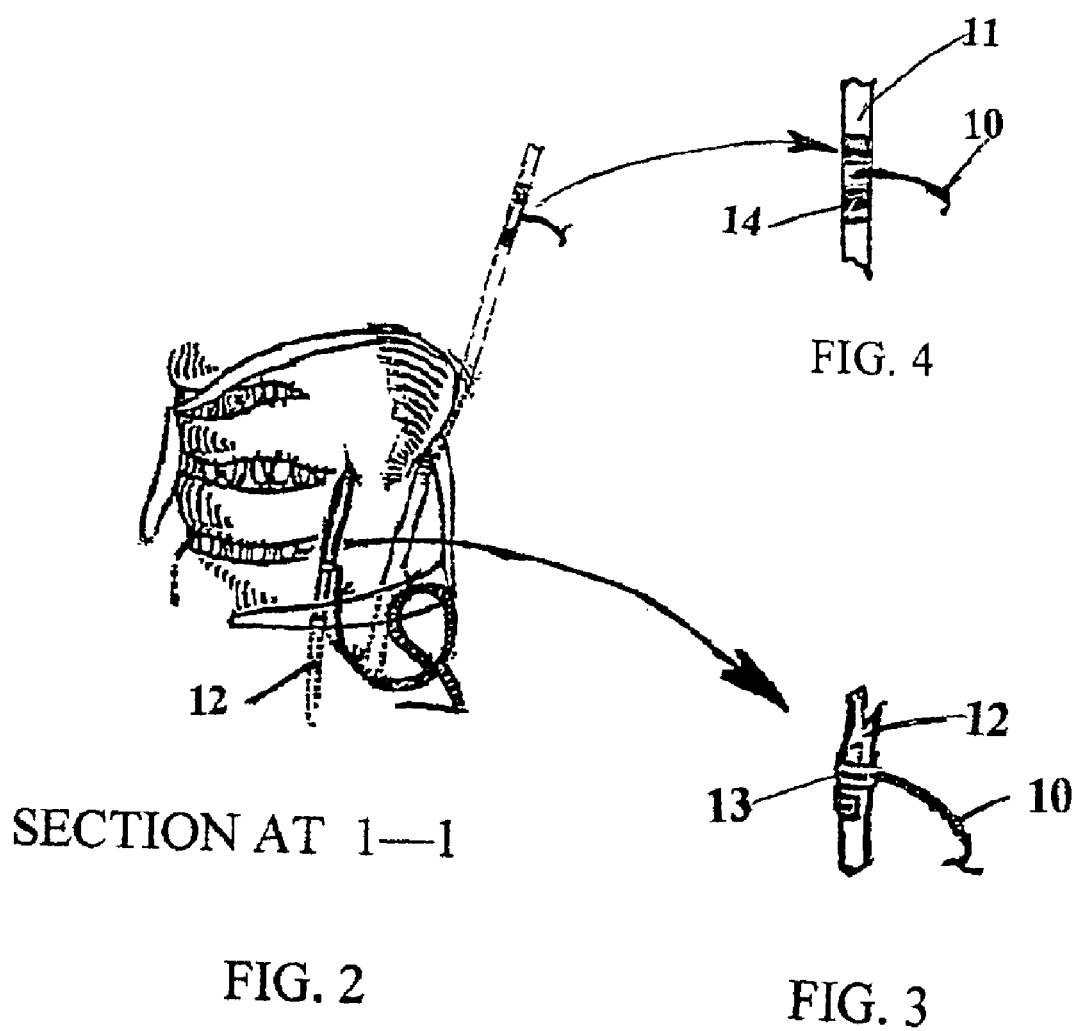
FIG. 2 shows a diagrammatic view of the attached perineural electrode near the tracheal wall.
FIG. 3 is a diagrammatic view illustrating the perineural electrode as wrapped around the RLN.
FIG. 4 is a diagrammatic view illustrating the perineural electrode as wrapped around the vagus nerve.

In FIG. 3 is a diagrammatic view illustrating the electrode lead (10) attached to the perineural electrode (13) as wrapped around the recurrent laryngeal nerve (12).

In FIG. 4 is a diagrammatic view illustrating the electrode lead (10) attached to the perineural electrode (14) as wrapped around the vagus nerve (11).

Alternative embodiments of practicing the invention, but within the spirit thereof, will in the light of this disclosure, occur to persons skilled in the art. It is intended that this description be taken as illustrative only and not be construed in any limiting sense except by the following claims.

The present invention is described by the following examples. Briefly, two stroke patients needing a tracheostomy were selected based on chronic aspiration verified by clinical and radiological criteria (videofluoroscopy also known as modified barium swallow [MBS]. The left recurrent laryngeal nerve was exposed and electrically stimulated to verify vocal fold adduction. Perineural electrodes available from Huntington Medical Research Institute were then implanted around the nerve. The electrical leads were tunneled and linked to an implantable receiver-stimulator available from Finetech placed subcutaneously on the chest wall. Activation of the stimulator was performed through an external transmitter linked by induction. The device was successfully triggered intra- and postoperatively. Serial flexible fiberoptic endoscopies and videofluoroscopies (MBS) demonstrated that aspiration is systematically arrested using low levels of electric stimulation (42 Hertz, 48–100 microseconds, 1 milliampere).

Criteria for patients' participation were as follows: 1) continuation or worsening of aspiration for at least six (6) weeks after the neurological insult and not alleviated by speech pathology management; 2) need for a tracheotomy, whether already in place or to be promptly done for pulmonary toilet; and 3) appropriate hand motor coordination to manipulate the external controller. Once these conditions were met, an institutional review board informed consent (Institutional Review Board Consent) was submitted, allowing the patients to be randomized. While standard therapy was planned in the first group considered as control, the other patients would receive an implanted stimulator. However, the FDA recently approved replacing the separate control group by a unique group of their own controls prior to surgery, since they failed standard non-invasive treatments. Testing will continue.

The first two patients, who fell into the original surgical category, included a healthy 54-year-old female nursing home resident who sustained a right hemispheric cerebrovascular accident (CVA, stroke) eight (8) years before her enrollment in the study. She had a left hemiparesis with expressive aphasia and some difficulty with maintaining an oral seal. Despite occasional seizures well controlled by phenytoin, she is a perceptive, intelligent woman involved in community activities with the other residents. Her history is remarkable for radiologically documented aspiration and several bouts of pneumonia for which she had not yet received a tracheotomy (at the time of enrollment). Videofluoroscopy (MBS) showed poor bolus formation and initiation of swallow with aspiration of barium (all consistencies) both silently and before and during the swallow. Based on these radiological as well as clinical findings (violent coughing spells during oral alimentation), she had received a pecutaneous endoscopic gastrostomy (PEG). Attempts to improve her swallowing by speech-language intervention were not successful.

The second patient is an 81-year-old male nursing home resident who sustained a left hemispheric cerebrovascular accident during cardiac bypass surgery followed by a tracheotomy 1 year before enrollment. He was also intelligent and had no impairment of his verbal skills. He possessed good hand motor coordination on the healthy side. While his MBS showed that he was able to close his mouth sufficiently to build pharyngeal pressure, he also presented with prolonged oral and pharyngeal transit time requiring multiple tongue thrusts to initiate the swallowing cascade. This resulted in considerable pooling and vallecular stasis. While puree mixture showed only laryngeal penetration, there was definite aspiration with honey-thick barium and liquids on the initial MBS.

Surgical technique differed only in terms of the prior existence of a tracheotomy that could potentially contaminate the wound. Both patients were placed in the supine position and after induction general anesthesia was continued through an endotracheal tube passed either transorally (first case) or through the preexisting tracheostoma (second case). In the first patient, the horizontal incision for the tracheotomy was laterally extended 5 cm on the left side until it reached the projection of the medial aspect of the sterocleidomastoid muscle. After satisfactory ventilation was verified, attention was turned to identifying the left recurrent laryngeal nerve (RLN) after dissection of the overlying soft tissue. However, care was exercised to start the horizontal incision 1 cm lateral to the second patient's tracheostoma to avoid contamination.

In the first patient, the RLN was sought at a distance from the larynx, after superomedial reflection of the thyroid lobe provided exposure at the root of the neck. In the second patient, however, the shorter incision and scarring lateral to the preexisting tracheostoma precluded peripheral exposure, and the nerve was initially identified at the inferior cornu of the thyroid cartilage after medial rotation of the larynx. The RLN was first stimulated with a commercially available handheld nerve stimulator (1 mA) (Varistim III, Clearwater, Fla.) to verify ipsilateral glottic fold adduction through transnasal flexible fiberoptic laryngoscopy. Then, the perineural electrodes were secured and motion was induced with an external stimulator (same intensity as above). The electrodes leads were then tacked to the neighboring soft tissues of the neck with Prolene 6-0 available from Ethicon, Johnson & Johnson, Somerville, N.J.

Attention was then turned to the chest wall where an incision was placed on the ipsilateral (left) side approximately 5 cm below the clavicle. A subcutaneous pocket was bluntly dissected over the fascia of the pectoralis major muscle. A tunnel was then created from the upper aspect of this pocket over the clavicle into the cervical field, creating a path between the wires and the pacemaker. The circuit was then connected to the electrode leads that were looped to avoid tension, and glottic adduction was again verified. The device was then placed into the subcutaneous pocket and glottic adduction was again verified by transcutaneous induction Closure used 3-0, and more superficially 4-0 Vicryl available from Ethicon, (Johnson & Johnson) and Steri-strips®, (available from 3M, St. Paul, Minn.), on the skin. The incision was closed with 3-0 subcutaneous and 4-0 subcuticular absorbable sutures and Steri-strips®. In the neck, the strap muscles were reapproximated with figure-of-eight 3-0 chromic catgut sutures. In the first patient, soft tissue was sutured to the tracheal stoma to wall off the nerve and electrode from possible contamination. The platysma, the subcutaneous tissue, and skin were also closed with absorbable sutures. The endotracheal tube was removed and replace with a 6-0 cuffed Shiley tracheostomy tube (available from Mallinckrodt, Inc., St. Louis, Mo.). The patients were directly returned to the surgical intensive care unit where vital signs were carefully monitored. Postoperative follow-up was uneventful. Both procedures were well tolerated with no immediate or delayed complications such as hematoma, infection, or wound breakdown. Chest radiographs confirmed the placement of pacemakers and perineural electrodes, no atelectasis, and normal position of the tracheotomy tubes. The patients were transferred to a regular floor on the second postoperative day.

The data acquisition protocol involved the following items to be checked weekly for 1 month, every 2 weeks for the following 2 months, and follow-up at 6 to 12 months: 1) vocal fold motion observed on a video screen by an endoscopist and other investigators present was recorded on tape during series of three regular bursts of stimulation. 2) Progress of the contrast material on the modified barium swallow before and during stimulation by the radiologist, speech pathologist, and the other investigators, and recorded to check either the presence of aspiration or its lack under conditions of stimulation previously used for vocal fold medialization. This evaluation was refined by submitting all fluoroscopic data to a blinded reviewer. 3) Paced and unpaced swallowing was also evaluated at the bedside by the speech-language pathologist and other investigators in terms of the presence or absence of colored material through the treacheal stoma; 4) Chest films were read by a staff radiologist. 5) Other objective data such as electrocardiogram and pulse oximetry were evaluated by direct readings by the investigators.

The barium swallows recorded in the first patient over a 6-month period were reviewed in random order by a qualified speech-language pathologist blinded to whether stimulation was on or off. Each swallow in its different phases was evaluated for aspiration. A statistical test of proportions evaluated the hypothesis that aspiration was reduced with stimulation on compared with stimulation off.

Observed results of the treatment follow. On the second operative-day, in the first patient, the external controller was programmed by trial and error to deliver square pulse trains necessary and sufficient (42 Hertz, 1milliampere, 56–132 microseconds) to product frank ipsilateral glottic closure, as monitored through flexible fiberoptic laryngoscopy. Stimulation generated no side effects such as neck tingling or discomfort, and no changes in electrocardiogram tracings and oxygen saturation measured by pulse oximetry. However, strong coughing spells occurred for pulse durations greater than 200 microseconds. The second patient requested to be endoscoped only after full recovery resulting from a fear that he would not tolerate the examination. When stimulation was done (on the seventh postoperative day), only occasional arytenoid adduction was noted with 42 Hertz, 1milliampere, even for pulse durations greater than 200 microseconds. On the $14^{th}$ postoperative day, however, frank motion returned, although stimulation intensity had to be slightly boosted. In both patients, vocal cord adduction was verified months after implantation.

The first patient's MBS on the fourth postoperative day confirmed severe aspiration in the absence of stimulation. However, with the current turned on (1 milliampere, 42 Hertz, 72–176 microseconds), the problem was checked as the bolus passed down through the esophagus in its entirety. A MBS done in the second patient after verification of glottic adduction ($14^{th}$ day) also showed that aspiration of liquids was arrested with the stimulation (1.5 milliamperes, 42 Hertz, 200 microseconds). In both patients, marked improvement of swallowing was verified months after implantation, based on viseofluoroscopy.

Fiberoptic and MBS evaluations initially repeated at weekly intervals confirmed the initial findings of blockage of aspiration at stimulating levels as low as those used during the initial, perioperative run in the first patient and smaller levels with the passage of time in the second subject.

The surgery and postoperative periods were well tolerated. Wound healing was excellent and there was no extrusion of the hardware. There was no pneumonia. The first patient experienced some problems unrelated to pacing. She had leakage of gastric juice from the PEG with abdominal skin irritation in the nursing home after two (2) months and tracheostomy dislodgement five (5) months postoperatively necessitating operative replacements. The parameters sufficient and necessary to effect dynamic laryngotracheal separation (1.0 milliamperes, 43Hertz, 56–132 microseconds) remained stable over time.

In the first patient, none of the three food consistencies (puree, thickened, and thin liquids) were substantially aspirated when stimulation was applied, as illustrated in Table 1 where significant difference between the outcomes of on and off stimulation are noted ($\alpha$ less than 0.01). Rather, aspiration occurred from premature entry into the laryngeal vestibule from laryngeal or vallecular residue. Considering the individual consistencies, there was significant reduction in aspiration for puree and thickened liquids, before and during the stimulated swallow, but not when stimulation was not applied (P less than 0.1). While thin liquids were almost universally aspirated before electrically stimulated (paced or unpaced) swallow, significant reduction occurred when it was applied (P less than 0.1). Finally, while stimulation did not significantly reduce aspiration for puree (the thickest consistency), it did so for the thickened and thick liquids (P less than 0.05).

TABLE I

Statistically Significant Differences as the Number of Aspiration/Total Number of Trials (proportion) on MBS for Paced and Nonpaced Swallows

| Symptoms | Puree | | | Thickened Liquid | | | Thin Liquid | | |
|---|---|---|---|---|---|---|---|---|---|
| | Stim off | Stim on | p | Stim off | Stim on | p | Stim off | Stim on | p |
| Aspiration prior to Swallow | 0/9 (0.000) | 1/12 (0.083) | 0.193 | 1/8 (0.000) | 1/13 (0.077) | 0.216 | 4/5 (0.800) | 3/8 (0.375) | 0.081 |
| Aspiration during Swallow | 0/9 (0.000) | 2/12 (0.167) | 0.107 | 3/8 (0.375) | 2/13 (0.154) | 0.131 | 1/5 (0.200) | 0/8 (0.000) | 0.107 |
| Aspiration after | 4/9 | 2/12 | 0.090 | 4/8 | 1/13 | 0.020 | 2/5 | 1/8 | 0.138 |

TABLE I-continued

Statistically Significant Differences as the Number of Aspiration/Total Number of Trials (proportion) on MBS for Paced and Nonpaced Swallows

| Symptoms | Puree | | | Thickened Liquid | | | Thin Liquid | | |
|---|---|---|---|---|---|---|---|---|---|
| | Stim off | Stim on | p | Stim off | Stim on | p | Stim off | Stim on | p |
| Swallow Aspiration during any phase of swallow (summary) | (0.444) 4/9 (0.444) | (0.167) 2/12 (0.333) | 0.305 | (0.500) 6/8 (0.750) | (0.077) 4/13 (0.308) | 0.032 | (0.400) 5/5 (1.000) | (0.125) 4/8 (0.500) | 0.042 |

The dynamic laryngotracheal closure system focuses on aspiration. It is an all-encompassing device completely bypassing an abolished function for which it provides a dynamic substitute. This invention makes use of the implantable receiver stimulator available from the Vocare system (NeuroControl Corp., Valley View, Ohio); the helical perineural electrodes are available from Huntington Medical Research Institute. The system is fully implantable and designed to implement glottic closure by transcutaneous induction through an external transmitter programmed by an external controller as used in the Vocare system.

Experiences with the two first patients have demonstrated excellent tolerance of the perineural electrodes, stimulator, and connecting wires available from Cyberonics Internal Data, Cyberonics, Houston, Tex. After prompt wound healing, no infection or extrusion occurred and the patients did not even feel the presence of the implanted material. Serial chest radiographs confirmed that the hardware had not moved, and there were no electrocardiogram or oxygen saturation changes under the stimulating conditions.

A tracheotomy was considered essential to the study 1) for pulmonary toilet, and 2) as a safety precaution against air hunger in an unlikely case of glottic blockage from circuit misfiring. Detrimental effects of this otherwise necessary intervention (limited laryngeal ascension by tethering the mobile airway to the cervical skin, reduced glottic adduction at rest from decreased reflexogenic activity) may be compounded by an unnatural ability of the patients to breathe during the swallowing effort. Additional observations will be made.

Swallowing is normally initiated according to a series of voluntary steps of the oral phase such as introduction of food in the mouth, mastication, posterior tongue thrusting, and so on. Once the bolus is present in the pharynx, however, the process becomes fully reflexogenic as it automatically proceeds until an end point represented by laryngeal closure and bolus diversion through the opening upper esophageal sphincter acting as a suction pump.

This short series has focused on voluntary intervention only as an intermediate step before implementing a fully automated artificial reflex arc. An accurate afferent sensor would allow the pool of candidates to be broadened to those who are either unwilling or incapable of initiating glottic control as a result of altered levels of consciousness or lack of residual bodily function.

Based on the two first cases it may be safely assumed that: 1) vocal fold pacing is an effective method for the control of aspiration; 2) the morbidity of this surgery is lower than that of traditional methods, and, 3) there is reasonable hope that with restored feedings through the natural paths, tracheotomies and PEGs may eventually become temporary bridges to a better means of rehabilitation.

Alternative embodiments of practicing the invention, but within the spirit thereof, will, in light of this disclosure, occur to persons skilled in the art it is intended that this description be taken as illustrative only, and not be construed in any sense except by the following claims.

I claim:

1. A method of treating dysphagia after administering general anesthesia to a human or animal utilizing electrical stimulation of a vagus nerve, a recurrent laryngeal nerve or both which comprises:
   a. performing a tracheotomy;
   b. identifying a vagus nerve or a recurrent laryngeal nerve or both by electrically stimulating said vagus nerve or said recurrent laryngeal nerve or both with a hand held electrical stimulator;
   c. dissecting the soft tissue overlying said vagus nerve, or said recurrent laryngeal nerve, or both;
   d. verifying glottic fold adduction by inserting a transnasal flexible fiberoptic laryngoscope;
   e. wrapping a perineural electrode around said vagus nerve or recurrent laryngeal nerve or both;
   f. inducing said glottic fold adduction by electrically stimulating said vagus nerve or said recurrent laryngeal nerve or both with a hand held electrical stimulator;
   g. verifying glottic fold adduction by means of said transnasal flexible fiberoptic laryngoscope;
   h. attaching said perineural electrode to neighboring soft tissue of the neck;
   i. making an incision on the side of said perineural electrode placement over said human's chest approximately 5 centimeters below human's clavicle;
   j. dissecting a subcutaneous pocket over said human's facia of the pectoralis major muscle;
   k. creating surgically a path between the upper aspect of said subcutaneous pocket over said clavicle into said cervical field for electric wires of said perineural electrode;
   l. implanting a receiver stimulator in said subcutaneous pocket;
   m. passing said electric wires from said perineural electrode through said path to said receiver stimulator;
   n. creating a looped section of said electrical wire to avoid any tension;
   o. wrapping said perineural electrode around said vagus nerve, or said recurrent laryngeal nerve, or both;
   p. inducing motion of said glottic folds by means of an external transmitter applied transcutaneously over the implanted receiver stimulator for verification of glottic fold motion prior to closing said incisions;
   q. closing said incisions at the subcutaneous pocket with absorbable sutures and adhesive strips; and
   r. confirming glottic fold motion by applying said electrical stimulation to said vagus nerve, said recurrent laryngeal nerve or both.

2. The method as defined in claim 1, step f wherein intensity of said electrical stimulation ranges from 0.1 to 2.0 milliamperes.

3. The method as defined in claim 2, wherein an output protector circuit limits said intensity of said electrical stimulation so as not to exceed 1 milliampere.

4. The method as defined in claim 1, step f wherein frequency of said electrical stimulation ranges from 20 to 60 Hertz.

5. The method as defined in claim 4, wherein frequency of said electrical stimulation is preferably 42 Hertz.

6. The method as defined in claim 1, step f wherein pulse duration ranges from 30 to 300 microseconds.

7. The method as defined in claim 6, wherein pulse duration is preferably 48 microseconds.

* * * * *